(12) United States Patent
Prasad et al.

(10) Patent No.: US 6,325,839 B1
(45) Date of Patent: Dec. 4, 2001

(54) METHOD FOR MANUFACTURING DENTAL RESTORATIONS

(75) Inventors: Arun Prasad, Cheshire; Gordon S. Cohen, Madison, both of CT (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/620,694

(22) Filed: Jul. 20, 2000

Related U.S. Application Data

(60) Provisional application No. 60/145,370, filed on Jul. 23, 1999.

(51) Int. Cl.[7] ................ C22C 5/00; B22F 3/12
(52) U.S. Cl. ................ 75/247; 419/36; 419/38
(58) Field of Search ............ 419/36, 38; 75/247

(56) References Cited

U.S. PATENT DOCUMENTS

| | | | |
|---|---|---|---|
| 4,273,580 | * | 6/1981 | Shoher et al. . |
| 4,459,112 | * | 7/1984 | Shoher et al. . |
| 4,492,579 | * | 1/1985 | Shoher et al. . |
| 4,742,861 | * | 5/1988 | Shoher et al. . |
| 4,797,100 | * | 1/1989 | Shoher et al. . |
| 4,814,008 | * | 3/1989 | Shoher et al. . |
| 4,828,495 | * | 5/1989 | Bell et al. . |
| 4,861,267 | * | 8/1989 | Shoher et al. . |
| 4,997,699 | * | 3/1991 | Shoher et al. . |
| 5,475,912 | * | 12/1995 | Sundstrom . |
| 5,613,849 | * | 3/1997 | Tanaka et al. . |
| 5,702,501 | * | 12/1997 | Osawa et al. ............ 75/255 |
| 5,773,099 | * | 12/1998 | Tanaka et al. ............ 427/529 |
| 5,808,280 | | 9/1998 | Apté et al. ............ 219/679 |
| 5,943,544 | * | 8/1999 | Morita et al. ............ 419/5 |
| 6,004,505 | | 12/1999 | Roy et al. ............ 419/6 |
| 6,066,290 | | 5/2000 | Dennis et al. ............ 419/38 |
| 6,183,689 | * | 2/2001 | Roy et al. ............ 419/38 |

* cited by examiner

Primary Examiner—Ngoclan Mai
(74) Attorney, Agent, or Firm—Ann M. Knab, Esq.

(57) ABSTRACT

Metal materials are sintered using microwave energy to provide high strength dental restorations. The metal materials used to manufacture the dental restorations herein are sintered to high density to provide high strength products that have a density close to the density achieved when the same materials are cast. A dense solid having a fine microstructure is achieved using microwave heating. Through the process described herein, higher heating rates may be achieved, reducing the time necessary for sintering the materials. The process is faster than conventional processes used in the manufacture of dental restorations, eliminates time-consuming steps typically involved in the lost wax process and provides materials with better grain-size control and properties. It is possible to produce high strength dental restorations at lower temperatures having high hardness and density and small grain size.

28 Claims, No Drawings

METHOD FOR MANUFACTURING DENTAL RESTORATIONS

CROSS-REFERENCE TO RELATED APPLICATIONS

This application claims priority to provisional application Ser. No. 60/145,370 filed Jul. 23, 1999 entitled Method For Manufacturing Dental Restorations which is hereby incorporated by reference.

FIELD OF THE INVENTION

The present invention relates generally to the manufacture of dental restorations and more specifically to the manufacture of dental restorations using microwave sintering processes.

BACKGROUND OF THE INVENTION

Currently, dental restorations may be made by sintering metal powders. Metal powders are usually mixed with a binder to assist in the shaping or injection molding of the restorations. These restorations are made in larger dimensions to accommodate shrinkage that occurs during the sintering process. The binder may be present in an amount of up to about twenty percent with the remainder of the mixture being the powder. Restorations made from the binder/powder mixture undergo a binder removal step that occurs in the preheating stage, followed by sintering at a suitable temperature and in a suitable atmosphere in conventional heating ovens. These steps require long processing times and impose poor control on dimensional tolerance.

It has been found that microwave sintering has been effective in the manufacture of machine parts such as drill bit inserts, as set forth in U.S. Pat. No. 6,066,290. The patent discloses drill bit inserts manufactured from tungsten carbide and cobalt. Sintering by microwave is accomplished in a short period of time leaving the integrity of the alloy unchanged. U.S. Pat. No. 6,004,505 is directed to a process and apparatus for the preparation of particulate or solid parts. Hard wear parts are made from tungsten carbide or silicon nitride particles that are packed into a mold or cavity and sintered in a microwave sintering apparatus. U.S. Pat. No. 5,808,282 discloses a microwave sintering process for ceramics, ceramic composites, and metal materials. The process involves surrounding the material with a granular susceptor bed, flowing a protective gas around the material, and irradiating the material and bed with microwave energy. The patent is directed to the sintering of cutting tools. None of the prior art address the sintering of certain powder metals used in the manufacture of dental restorations.

It is beneficial to reduce the processing and sintering time required in the manufacture dental restorations. It is desirable to be able to better control the properties of dental restorations during manufacture thereof.

SUMMARY OF THE INVENTION

These and other objects and advantages are accomplished by the process of the present invention wherein metal materials are sintered using microwave energy to provide high strength dental restorations. The metal materials used to manufacture the dental restorations herein are sintered to high density to provide high strength products that have a density close to the density achieved when the same materials are cast. A dense solid having a fine microstructure is achieved using microwave heating. Through the process described herein, higher heating rates may be achieved, reducing the time necessary for sintering the materials. The process is faster than conventional processes used in the manufacture of dental restorations, eliminates time-consuming steps typically involved in the lost wax process and provides materials with better grain-size control and properties. It is possible to produce high strength dental restorations at lower temperatures having high hardness and density and small grain size.

DESCRIPTION OF THE INVENTION

As will be appreciated, metal materials are sintered using microwave energy to provide high strength dental restorations. The process is broadly applicable to the manufacture of all types of dental restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors.

In one embodiment herein, metal powder in combination with a vehicle is used to manufacture a dental restoration. The vehicle is preferably a binder material used to hold the metal particles together. The combination metal powder/binder is preferably in a paste or sheet form. Accordingly, the paste may be pressed onto and around the die or the sheet may be cut to a desired shape to fit onto the die. The die is typically a model of a tooth or teeth to be restored. Alternately, the metal powder may be packed into a mold without a binder or with the addition of a binder to assist in holding the metal particles together.

Materials and methods useful herein for the fabrication and preparation of materials for the manufacture of a dental restoration prior to sintering are disclosed in commonly owned, copending provisional application Ser. Nos. 60/175, 361 filed Jan. 10, 2000, 60/182,388 filed Feb. 14, 2000, 60/182,155 filed Feb. 14, 2000, 60/193,591 filed Mar. 30, 2000, and 60/201,067 filed May 1, 2000 which are all hereby incorporated by reference. U.S. Pat. Nos. 4,997,699, 4,814,008, 4,742,861, and 4,828,495 further discuss materials and fabrication techniques for the preparation of dental restorations and hereby are incorporated by reference.

Any metal or alloy used in the manufacture of dental restorations may be used in the process herein. The metal powder is preferably a high fusing metal and may comprise one or more precious metals, non-precious metals and alloys thereof. Preferably, the metal powder comprises a non-oxidizing metal. More preferably, the metal powder is selected from one or more of gold, platinum, silver and alloys thereof whereby the alloys may comprise one or more of the metals in combination with one another and/or with a different metal, such as copper, rhodium, palladium, indium, tin, gallium, germanium, cobalt, chromium, iron and mixtures thereof. One preferred alloy comprises about 85 to about 99% Au, 0 to about 15% Pt, and 0 to about 15% of one or more of Ga, Zn, Ge, Cu, Sn Ag, Pd, Rh, In, Ru, and Ta. The particle size of the powder is in the range of about 0.1 to about 150 microns and preferably from about 0.1 to about 40 microns.

Typical binder materials include, but are not limited to filler-free wax, ammonium caseinate, ammonium stearate, pectin, hexamine, ethyl cellulose, anthracene, triacetyl starch, dulcin, carbazole and tetraphenyl ethylene. The binder may be mixed with a solvent prior to mixing with the metal powder. Solvents include, without limitation, propylene glycol, water, eugenol, light paraffin oil, butyl acetate, butyl benzoate, diacetone alcohol, and dibutyl phthalate. The binder and solvent are driven off during the sintering process.

The powder/ binder mixture comprises about 75 to about 100 percent powder and about 0 to about 25 percent binder and preferably about 90 to about 99 percent powder and about 1 to about 10 percent binder. Preferably, the powder is present in about 96 percent by weight and the binder is present in about 4 percent by weight. Examples of commercially available metal materials useful herein include SinterKor™ 90⁺Pt sheets and SinterKor™ 24 kt sheets, each available from Jeneric/Pentron Inc., Wallingford, Conn.

In an alternate embodiment, the metal may be in the form of a thin metal foil containing one or more of gold, platinum, silver and alloys thereof whereby the alloys may comprise one or more of the metals in combination with one another or with a different metal, such as copper, rhodium, palladium, indium, tin, gallium, ruthenium, germanium, cobat, chromium, iron and mixtures thereof. U.S. Pat. Nos. 4,492,579, 4,797,100, 4,273,580, 4,861,267 and 4,459,112 are directed to dental restorations fabricated from metal foils and are hereby incorporated by reference.

After the material has been modeled onto the die, molded to the desired form or inserted into a mold, the model created is ready for firing. The model is sintered in a microwave atmosphere to provide a high strength metal restoration. The sintering process takes place in a microwave apparatus which is similar to a conventional porcelain oven, but which supplies microwave energy to sinter the materials placed therein. Examples of microwave devices useful herein include those described in U.S. Pat. Nos. 6,066,290, 6,004,505, and 5,808,282 which are hereby incorporated by reference.

The sintering range depends upon the metal or alloy being used. The sintering temperature is close to the melting temperature of the metal/alloy. Preferably, the sintering temperature is below the melting temperature of the metal or alloy being sintered. Typically, the sintering range is about 800 to about 1200° C. The microwave heating can be accomplished in air or in a controlled atmosphere such as in an argon, nitrogen or similar atmosphere. The sintering time will vary depending on the cross-sectional area of the restoration. For example, a dental crown of very thin cross-section will take less time than for example, a pontic or bridge that has a thicker cross-section. The sintering time could be as low as about one minute to about ten or twenty minutes or as high as thirty minutes to one to two hours.

After the sintering process is complete, the dental restoration is removed from the mold or die and a ceramic or porcelain material is applied to the sintered metal layer. The porcelain is preferably an opaque porcelain such as Synspar® Opaque porcelain available from Jeneric/Pentron Inc., Wallingford, Conn. used in the manufacture of dental restorations, although any porcelain with an appropriate coefficient of thermal expansion which is compatible with the underlying metal may be used herein to achieve the final result.

The model with the metal and opaque porcelain thereon is thereafter sintered to obtain a dental restoration. The sintering may be carried out in a microwave apparatus or in a conventional porcelain oven such as the JP 1200™ furnace and the AutoPress® Plus™ furnace, each available from Jeneric/Pentron Inc., Wallingford, Conn.

The metal materials used to manufacture the dental restorations herein are sintered to high density to provide high strength products that have a density close to the density achieved when the same materials are cast. A dense solid having a fine microstructure is achieved using microwave heating. Through the process described herein, higher heating rates may be achieved, reducing the time necessary for sintering the materials. The process is faster than conventional processes used in the manufacture of dental restorations, eliminates time consuming steps typically involved in lost wax process and provides material with better grain-size control and properties. It is possible to produce high strength dental restorations at lower temperatures having high hardness and density and small grain size.

The following examples illustrate the invention.

EXAMPLE 1

A rectangular piece of Captek™ Foil G (available from Precious Chemicals, Ltd., Longwood, Fla.) was placed on Captek Foil P and subjected to a sintering temperature of 1080° C. for 20 minutes in a microwave oven developed at Materials Research Laboratory at the Pennsylvania State University, University Park, Pa (MRL). Foil P & Foil G are strips of materials produced from a blend of a proprietary alloy and gold, respectively, with a volatile binder. Since the metallic ingredients of these strips are of non-oxidizing type, sintering was conducted in air.

The results showed complete removal of binders and partial sintering of both the foils. The foils were welded to each other and could not be separated with a scalpel.

EXAMPLE 2

Foil G and Foil P used in Example 1 above were subjected to a sintering temperature of 1120° C. for 20 minutes. The results showed Foil G had melted and infiltrated into Foil P.

EXAMPLE 3

Powder of an alloy, Bio-86™ (available from Jeneric/Pentron Inc., Wallingford, Conn.) was compacted into pellets using a pressing machine. Bio-86 is a high noble ceramic alloy (oxidizing type) having the following composition:

| | | |
|---|---|---|
| Au = 85.9% | Pt = 11% | Mn = 1% |
| Ta = 1% | In = 0.5% | Zn = 0.5% |
| Ir + CaB$_6$ = Balance | | |

The following pellets were then subjected to sintering in a microwave oven using the following parameters. The atmosphere used around the pellet was forming gas.

A. Bio-86™, sintered at 900° C. for 10 minutes.
B. Bio-86™, sintered at 850° C. for 10 minutes.
C. Bio-86™, sintered at 780° C. for 10 minutes.
D. Bio-86™ in C above was sintered again at 780° C. for 10 minutes.

Pellets A and B were molten and changed from their original shape to a sphere. Pellets C and D were sintered and retained their shapes. They had higher density in comparison to the starting pellets. There was no oxidation during sintering.

The above examples illustrate that metal materials typically used in the fabrication of dental restorations may be used in the sintering process described herein to achieve sintered high strength materials useful as dental restorations.

In accordance with another embodiment of the present invention, the sintering process may be used in the manufacture of jewelry parts. The jewelry parts, including but not limited to rings, earrings, necklaces and bracelets, may be fabricated of metal powders with or without a binder and molded into desired shapes. The parts may be sintered in a microwave apparatus as discussed above for dental restorations. The process reduces processing and manufacturing time. Depending on the thickness of the cross-sectional area and the sintering temperature, the sintering time will vary with each piece. As with dental restorations, sintering may take place from one minute to thirty minutes, or from thirty minutes to two hours.

While various descriptions of the present invention are described above, it should be understood that the various features can be used singly or in any combination thereof Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A process for manufacturing a dental restoration comprising:

forming metal powder into a shape of a dental restoration; and microwave sintering the shaped powder to form the dental restoration.

2. The process of claim 1 wherein the metal powder comprises one or more metal alloys.

3. The process of claim 1 wherein the dental restoration is selected from an orthodontic appliance, bridge, space maintainer, tooth replacement appliance, splint, crown, partial crown, denture, post, tooth, jacket, inlay, onlay, facing, veneer, facet, implant, abutment, cylinder, and connector.

4. The process of claim 1 wherein the metal powder comprises a non-oxidizing metal.

5. The process of claim 4 wherein the non-oxidizing metal is selected from one or more precious metals and alloys thereof.

6. The process of claim 1 wherein the metal powder is selected from one or more of gold, platinum, silver and alloys thereof.

7. The process of claim 1 wherein the metal powder comprises an oxidizing metal or alloy thereof.

8. The process of claim 1 wherein the metal powder is mixed with a binder to form a metal powder/binder mixture prior to forming into a shape of a dental restoration.

9. The process of claim 8 wherein the metal powder is present in an amount of about 90 to about 99 percent by weight and the binder is present in an amount of about 1 to about 10 percent by weight of the mixture.

10. The process of claim 8 wherein the binder is selected from wax, ammonium caseinate, ammonium stearate, pectin, hexamine, ethyl cellulose, anthracene, triacetyl starch, dulcin, carbazole and tetraphenyl ethylene.

11. The process of claim 1 wherein microwave sintering is conducted in the temperature range of about 800 to about 1200° C.

12. The process of claim 1 wherein the microwave sintering is conducted in a controlled atmosphere.

13. The process of claim 1 wherein forming the metal powder into a shape of a dental restoration comprises:

forming a model of one or more teeth; and coating the model with metal powder.

14. The process of claim 1 wherein forming the metal powder into a shape of a dental restoration comprises:

forming a mold to the shape of the dental restoration; and filling the mold with metal powder.

15. A dental restoration manufactured by the process comprising:

forming metal powder into a shape of a dental restoration; and microwave sintering the shaped powder to form the dental restoration.

16. The dental restoration of claim 15 wherein the metal powder comprises one or more metal alloys.

17. The dental restoration of claim 15 comprises a restoration selected from an orthodontic appliance, bridge, space maintainer, tooth replacement appliance, splint, crown, partial crown, denture, post, tooth, jacket, inlay, onlay, facing, veneer, facet, implant, abutment, cylinder, and connector.

18. The dental restoration of claim 15 wherein the metal powder comprises a non-oxidizing metal.

19. The dental restoration of claim 15 wherein the non-oxidizing metal is selected from one or more precious metals and alloys thereof.

20. The dental restoration of claim 15 wherein the metal powder is selected from one or more of gold, platinum, silver and alloys thereof.

21. The dental restoration of claim 15 wherein the metal powder comprises an oxidizing metal or alloy thereof.

22. The dental restoration of claim 15 wherein the metal powder is mixed with a binder to form a metal powder/binder mixture prior to forming into a shape of a dental restoration.

23. The dental restoration of claim 15 wherein the metal powder is present in an amount of about 90 to about 99 percent by weight and the binder is present in an amount of about 1 to about 10 percent by weight of the mixture.

24. The dental restoration of claim 23 wherein the binder is selected from wax, ammonium caseinate, ammonium stearate, pectin, hexamine, ethyl cellulose, anthracene, triacetyl starch, dulcin, carbazole and tetraphenyl ethylene.

25. The dental restoration of claim 15 wherein microwave sintering is conducted in the temperature range of about 800 to about 1200° C.

26. The dental restoration of claim 15 wherein the microwave sintering is conducted in a controlled atmosphere.

27. The dental restoration of claim 15 wherein forming the metal powder into a shape of a dental restoration comprises:

forming a model of one or more teeth; and coating the model with metal powder.

28. The dental restoration of claim 15 wherein forming the metal powder into a shape of a dental restoration comprises:

forming a mold to the shape of the dental restoration; and filling the mold with metal powder.

* * * * *